United States Patent [19]

Kuehne

[11] 4,283,536
[45] * Aug. 11, 1981

[54] PREPARATION OF VINCADIFFORMINE AND RELATED DERIVATIVES

[75] Inventor: Martin E. Kuehne, Burlington, Vt.

[73] Assignee: University of Vermont, Burlington, Vt.

[ * ] Notice: The portion of the term of this patent subsequent to May 15, 1996, has been disclaimed.

[21] Appl. No.: 34,792

[22] Filed: Apr. 30, 1979

Related U.S. Application Data

[63] Continuation-in-part of Ser. No. 865,657, Dec. 29, 1977, Pat. No. 4,154,943.

[51] Int. Cl.³ .................. C07D 471/14; C07D 487/04
[52] U.S. Cl. .................. 546/51; 260/245.7; 260/326.5 B; 260/326.37; 260/326.9; 260/343.5; 260/348.57; 260/348.58; 546/223; 560/226; 568/484; 568/495
[58] Field of Search .................. 546/51; 260/326.37, 260/245.7

[56] References Cited

U.S. PATENT DOCUMENTS

| | | | |
|---|---|---|---|
| 3,525,750 | 8/1970 | Renner | 260/245.7 |
| 4,146,643 | 3/1979 | Pfäffli | 424/262 |
| 4,154,943 | 5/1979 | Kuehne | 546/51 |
| 4,220,774 | 9/1980 | Kuehne | 546/51 |

OTHER PUBLICATIONS

Kuehne et al., (I), J. Org. Chem., vol. 43, No. 19, pp. 3702-3704, (9/15/78).
Kuehne et al., (II), J. Org. Chem., vol. 43, No. 19, pp. 3705-3710, (9/15/78).
Kuehne et al., (III), J. Org. Chem., vol. 44, No. 7, pp. 1063-1068, (3/30/79).
Wang, Dissertation Abstracts, vol. 26, (3), p. 1361, (1965).
March, "Advanced Organic Chemistry", (1968), pp. 667, 668, 671.

*Primary Examiner*—Donald G. Daus
*Assistant Examiner*—Diana G. Rivers
*Attorney, Agent, or Firm*—Pollock, Vande Sande & Priddy

[57] ABSTRACT

This invention relates to the preparation of vincadifformine and related derivatives which are useful as starting material for the synthesis of among other alkaloids vincamine and other similar compounds possessing interesting psychopharmacologic properties.

A tetrahydro-β-carboline (II) is reacted with benzoyl chloride to provide a 2-benzoyl-1,2,3,4-tetrahydro-9H-pyrido-(3,4-b)-indole (III). Then compound (III) is reduced to give a 2-benzyl-1,2,3,4-tetrahydro-9H-pyrido-(3,4-b)-indole (IV). Thereafter, compound (IV) is transformed by t-butyl hypochlorite into a chloroindolenine derivative (V) which is immediately treated with a metal dialkylmalonate such as thallium t-butyl methyl malonate to give a dialkyl 3-benzyl-1,2,3,4,5,6-hexahydroazepino-(4,5-b)-indole-5,5-dicarboxylate (VI). Compound (VI) is then partly decarboxylated into a alkyl 3-benzyl-1,2,3,4,5,6-hexahydro-(4,5-b) indole-5-carboxylate (VII). Compound (VII) is hydrogenated to give an alkyl 1,2,3,4,5,6-hexahydroazepino-(4,5-b)-indole 5-carboxylate (VIII). In an alternative embodiment, compound (VI) can be hydrogenated to the corresponding dialkyl 1,2,3,4,5,6-hexahydroazepino-(4,5-b)-indole-5,5-dicarboxylate which is then decarboxylated into compound (VIII). Compound (VIII) is condensed with a functionalised aldehyde, typically a epoxy aldehyde or a haloaldehyde such as 1-bromo-4-formylhexane, to give vincadifformine or similar pentacyclic derivatives.

24 Claims, No Drawings

PREPARATION OF VINCADIFFORMINE AND RELATED DERIVATIVES

The invention described herein was made in the course of work under a grant from the Department of Health, Education and Welfare.

This is a continuation in part of my copending U.S. patent application Ser. No. 865,657, filed Dec. 29, 1977, and now U.S. Pat. No. 4,154,943.

The present invention relates to a synthesis process for vincadifformine and similar useful polycyclic derivatives.

The compounds prepared by the process of the invention are of the general formula I.

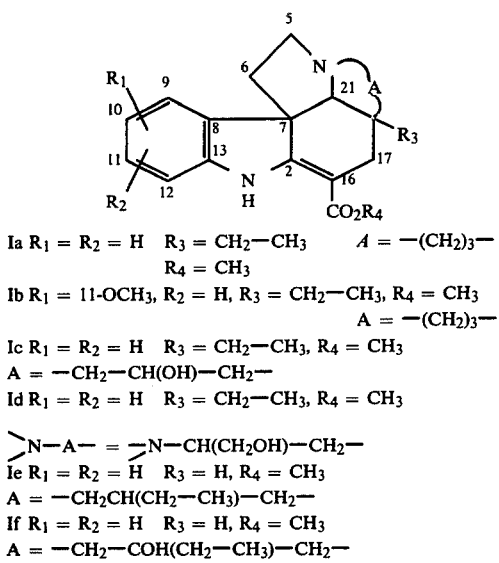

Ia $R_1 = R_2 = H$  $R_3 = CH_2—CH_3$  $A = —(CH_2)_3—$
$R_4 = CH_3$

Ib $R_1 = 11\text{-}OCH_3$, $R_2 = H$, $R_3 = CH_2—CH_3$, $R_4 = CH_3$
$A = —(CH_2)_3—$ Ic $R_1 = R_2 = H$  $R_3 = CH_2—CH_3$, $R_4 = CH_3$
$A = —CH_2—CH(OH)—CH_2—$ Id $R_1 = R_2 = H$  $R_3 = CH_2—CH_3$, $R_4 = CH_3$ $>N—A— = —N—CH(CH_2OH)—CH_2—$
Ie $R_1 = R_2 = H$  $R_3 = H$, $R_4 = CH_3$
$A = —CH_2CH(CH_2—CH_3)—CH_2—$ If $R_1 = R_2 = H$  $R_3 = H$, $R_4 = CH_3$
$A = —CH_2—COH(CH_2—CH_3)—CH_2—$ In the above general formula, $R_1$ and $R_2$ are the same or different, being selected from the group consisting of hydrogen, hydroxy, acyloxy, carbamate, halo, lower alkoxy or alkyl radical, $R_3$ and $R_4$ are lower alkyl or hydrogen, or a combination of such radicals. A represents an alkyl chain, or unsaturated aliphatic hydrocarbon chain, containing from 1 to 7 carbon atoms and which may be substituted by one or more alkyl, hydroxy or hydroxy-alkyl radicals.

The term "lower alkyl" as used herein contemplates saturated hydrocarbon radicals, branched or not, containing from one to seven carbon atoms.

Examples of compounds which are prepared in accordance with the present invention are those of formulae Ia, Ib, Ic, Id, Ie and If as defined hereabove.

The numbering of vincadifformine and its derivatives is in accordance with Le Men and Taylor, Experientia 1965, 21, 508.

Vincadifformine of the formula Ia is an alkaloid which is the raw material for the preparation of the vincamine group alcaloids as described in Belgian Pat. No. 772,005 and No. 848,475.

Vincamine and some of its derivatives are well-known alkaloids used in human therapeutics as psychotropic drugs of high efficiency and possessing a relatively low order of toxicity.

Furthermore, it has been shown that the rearrangement of vincadifformine leading to vincamine may be applied to a large number of other similar derivatives to provide vincamine related compounds (see French patent applications No. 76 22335, No. 76 22275, Belgian Patent No. 816,692 and U.S. patent application Ser. No. 968,147 filed on Dec. 11th, 1978 in the name of J. Hannart).

For example, 10-bromo vincamine and 10-bromo vincamone are compounds superior to vincamine when the test of hypoxic anoxia with mice is applied. These compounds can easily be obtained from the corresponding 10-bromo vincadifformine.

Two total synthetic methods for vincadifformine are already described in the literature by J. Kutney et al, J. Amer. Chem. Soc. 90, 3891, 1968 and J. V. Laronze et al, Tetrahedron Letters 491, 1974.

11-methoxy vincadifformine (ervinceine) of the formula Ib is an alkaloid occuring in Vinca Erecta and described by D. A. Rakhimov, V. M. Malikov, M. R. Yagudaev and S. N. Yunusov (Khim, prir.Soedin. 226, 1970).

Alkylation of ervinceine yields the corresponding N(a) methyl derivative. One enantiomer of this compound, obtained by degradation of vindoline, has recently been converted back to vindoline, the indoline moiety of the "dimeric" oncolytic alkaloid vincaleukoblastine (J. P. Kutney et al. J. Am. Chem. Soc. 100, 4220 (1978).

Pseudo-vincadifformine of formula Ie is an alkaloid occuring in different Apocynacea and which has been obtained by hemisynthesis (J. P. Kutney, E. Piers and R. T. Brown, J. Amer. Chem. Soc. 92, 1700, 1970).

Pandoline of formula If can be obtained from certain plants of the genus Pandaca (M. Zeches, M. M. Debray, G. Ledouble, L. Lemen-Olivier and J. Le Men Phytochemistry 14 1122, 1975). No total synthesis of this rare alkaloid has been reported.

The present invention aims to obtain vincamine and related polycyclic compounds with high yields, reducing the number of intermediate steps and using cheap reagents.

The invention can be distinguished more particularly by the fact that in a first step a tetrahydro-β-carboline (II) when treated with benzoyl chloride yields a 2-benzoyl-1,2,3,4-tetrahydro-9H-pyrido-[3,4b]-indole (III).

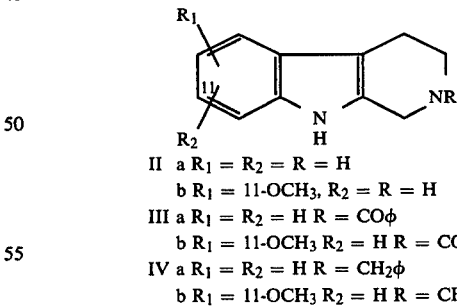

II a $R_1 = R_2 = R = H$
b $R_1 = 11\text{-}OCH_3$, $R_2 = R = H$
III a $R_1 = R_2 = H$ $R = CO\phi$
b $R_1 = 11\text{-}OCH_3$ $R_2 = H$ $R = CO\phi$
IV a $R_1 = R_2 = H$ $R = CH_2\phi$
b $R_1 = 11\text{-}OCH_3$ $R_2 = H$ $R = CH_2\phi$ wherein $R_1$ and $R_2$ have the same meaning as described above and $\phi$ represents a phenyl radical.

In a second step, the reduction of III by a reducing agent such as lithium aluminium hydride (LAH) in tetrahydrofuran (THF), yields the corresponding 2-benzyl-1,2,3,4-tetrahydro-9H-pyrido(3,4-b) indole IV.

In a third step, derivative IV is transformed by the action of tertisobutyl hypochlorite or a similar chlorinating agent into a chloroindolenine (V) which is immediately treated with a dialkyl thallium or sodium malonate or analogous compound, preferably t-butyl methyl thallium malonate

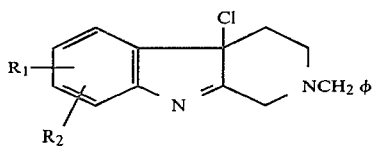

Va $R_1 = R_2 = H$
Vb $R_1 = 11\text{-OCH}_3$ $R_2 = H$ to yield a 3-benzyl-1,2,3,4,5,6-hexahydroazepino (4,5-b) indole-5,5-di(alkyl carboxylate) derivative of the formula VI

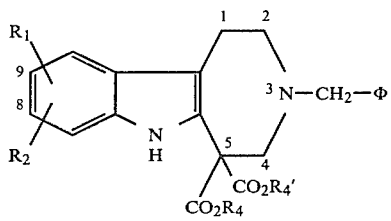

VIa $R_1 = R_2 = H$ $R_4 = CH_3$ $R_4' = $ t-butyl
VIb $R_1 = 8\text{-OCH}_3$, $R_2 = H$, $R_4 = R_4' = CH_3$
VIc $R_1 = R_2 = H$ $R_4 = R_4' = CH_3$ wherein $R_1$, $R_2$ and $R_4$ are as defined above. $R_4'$ is a lower alkyl group, typically a methyl, ethyl or t-butyl radical.

For this condensation, any solvent inert to the reaction conditions may be used. Benzene and toluene are especially convenient and practical for this use.

In a fourth step, derivative VI is partly decarboxylated into an alkyl 3-benzyl-1,2,3,4,5,6-hexahydroazepino-(4,5-b)-indole-5-carboxylate (VII).

For example, in the case of a t-butyl methyl dicarboxylate, this transformation is best achieved by means of trifluoroacetic anhydride or trifluoroacetic acid. In the case of the corresponding dimethyl derivative, monodecarbomethoxylation is achieved by lithium chloride in dimethylformamide.

In a fifth step, derivative VII is hydrogenated in the presence of a catalyst, typically 5% Pd on charcoal, to remove the protecting benzyl group, yielding an alkyl 1,2,3,4,5,6-hexahydroazepino(4,5-b) indole-5-carboxylate derivative of the general formula VII

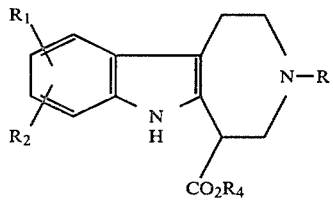

VII R = $CH_2\phi$
VIIa $R_1 = R_2 = H$ $R_4 = CH_3$
VIIb $R_1 = 8\text{-OCH}_3$ $R_2 = H$ $R_4 = CH_3$
VIII R = H
VIIIa $R_1 = R_2 = H$ $R_4 = CH_3$
VIIIb $R_1 = 8\text{-OCH}_3$, $R_2 = H$ $R_4 = CH_3$ In an alternative of the invention, product VI can be hydrogenated in presence of Pd/C at 5% to yield a dialkyl-1,2,3,4,5,6-hexahydroazepino(4,5-b)-indole-5,5-dicarboxylate (VI')

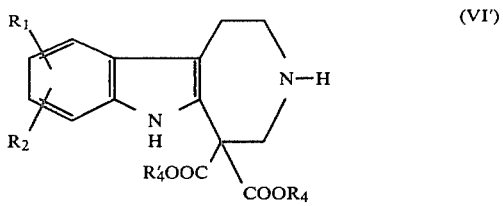

which is then partly decarbomethoxylated into VIII.

In a sixth step, derivative VII is condensed with a functionalised aldehyde IX yielding vincadifformine or related derivatives of formula (I).

By functionalised aldehyde it is understood an aldehyde for which a corresponding tertiary enamine derivative may be N-alkylated intra-molecularly, to form an enammonium salt.

Typically such compounds are halo, aryl or alkylsulfoxy, or epoxy aldehydes having three to fourteen carbon atoms.

Examples of such aldehydes are IXa, IXb, IXc, IXd and IXe

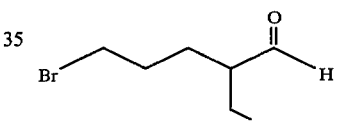

IXa

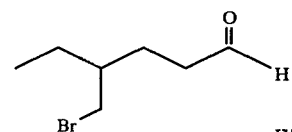

IXb

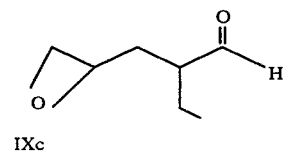

IXc

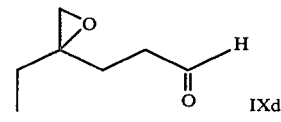

IXd

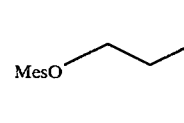

IXe

MesO = mesyloxy

In the case of the reaction of a haloaldehyde with the azepinoindole VIII, the intermediate cyclic enammonium of general formula X has been postulated.

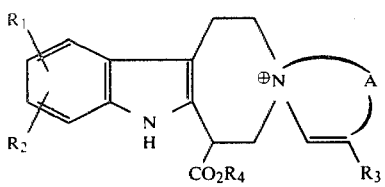

In effecting the condensation (VIII+aldehyde through X) it has been found preferable to use a solvent such as dry methanol, but other inert solvents to the reaction conditions, for example dry benzene, may be used.

The temperature of the reaction may vary from −20° C. to the boiling point of the reaction medium. Preferred temperature ranges include 20° to 40° C.

5-bromo-2-ethylpentanal (IXa) which can be used in the last step of the vincadifformine synthesis may be prepared following a new process, hereunder described, which is both practical and convenient.

One acetalyses methyl or ethyl 4-formylhexanoate to yield respectively methyl 4-dimethoxymethylhexanoate or ethyl 4-diethoxymethylhexanoate which is reduced by means of lithium aluminium hydride into respectively 4-dimethoxymethyl-1-hexanol or 4-diethoxymethyl-1-hexanol.

The alcohol obtained in this way is dehydroxybrominated yielding respectively 1-bromo-4-dimethoxymethyl-hexane and 1-bromo-4-diethoxymethyl-hexane, which is hydrolysed to yield the required 1-bromo-4-formylhexane or 5-bromo-2-ethylpentanal.

Another preparation of 5-bromo-2-ethylpentanal is also disclosed in W. Oppolzer, H. Hauth, P. Pfaffli, R. Wenger, Helv. 60, 1861 (1977).

In the case of the pandoline and epipandoline synthesis, the adequate functionalised aldehyde IXd is obtained following the reactional sequence of scheme I, which is described in details in the examples.

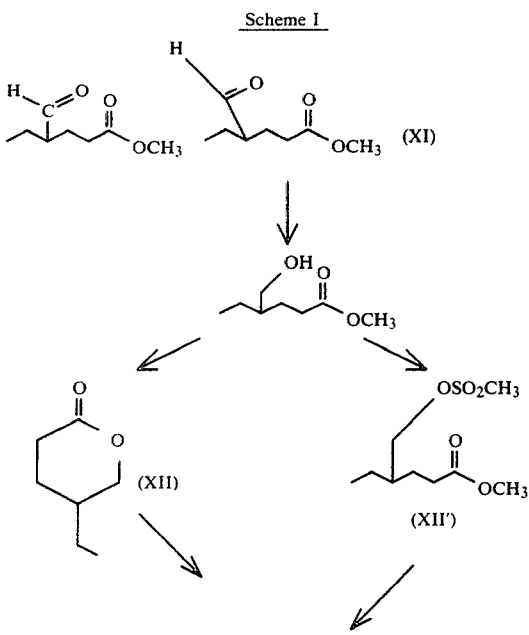

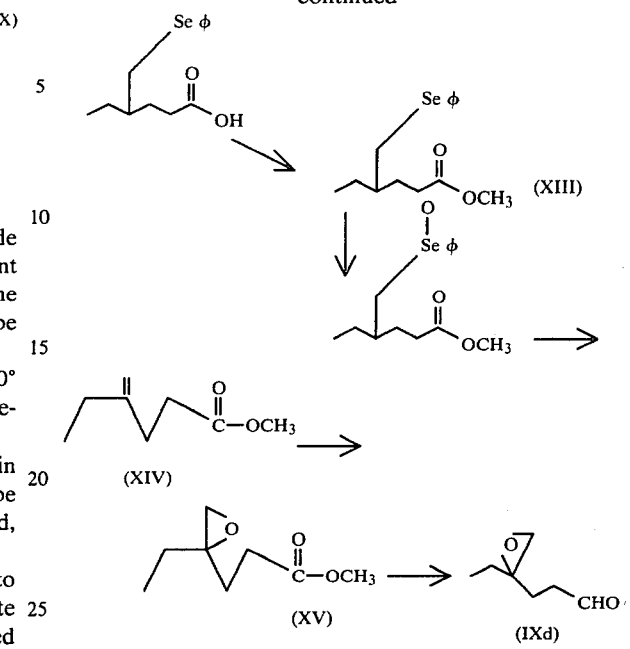

Procedures for the preparation of other useful functionalised aldehydes are given in the examples.

The following examples describe the characteristics of the invention in a non limitative way.

EXAMPLE 1

2-benzoyl-1,2,3,4-tetrahydro-9H-pyrido-[3,4b]-indole (IIIa)

Tetrahydro-β-carboline (IIa) (3 g, 17.44 mmol) was suspended in dry benzene (50 ml) and pyridine (20 ml). Benzoyl chloride (3 ml, 25.8 mmol) was added dropwise, with stirring at room temperature. After addition was complete the mixture was heated at 70° C. for 1 hour.

The hot mixture was then poured into 200 ml of water and the layers separated. The water layer was washed with benzene (2×50 ml) and the combined organic phases were washed with water (2×25 ml), 1 N HCl (2×20 ml), water (20 ml) and (saturated) sodium bicarbonate (2×20 ml).

The solvent was evaporated and the residual brown oil dissolved in 10 ml of benzene. Hexane (60 ml) was slowly added with scratching to induce crystallization. Pure benzoylated amine was obtained (4.57 g, 95%). Recrystallization from aqueous ethanol gave white needles.

mp: 156°–157° C. IR (CHCl$_3$): 3470, 3060, 3020, 2925, 2860, 1625, 1620, 1575, 1490, 1460, 1435, 1305, 1205, 1150, 1045, 1025, 980 cm$^{-1}$

NMR (CDCl$_3$): δ2.80 (bs, 2 H), 3.65 (bs, 2 H), 4.8 (bs, 2 H) 7.0–7.30 (m, 9 H), 8.75 (bs, 1 H)

Mass spectrum: (80 eV) m/e (rel intensity) 276 (M+, 8), 262 (16), 168 (15), 143 (100), 105 (15), 91 (21), 77 (16), 44 (44), 40 (71)

Analysis calculated for C$_{18}$H$_{16}$N$_2$O: C, 78.24; H, 5.84; N, 10.14; found: C, 78.24; H, 5.92; N, 10.18

EXAMPLE 2

2-benzyl-1,2,3,4-tetrahydro-9H-pyrido-[3,4b]-indole (IVa)

To a solution of lithium aluminum hydride (1 g, 26.3 mmol) in 100 ml of dry THF at room temperature was added a solution of N-benzoyltetrahydro-$\beta$-carboline (IIIa) (4.5 g, 16.3 mmol) in 100 ml of dry THF over 15 min.

The stirred solution was refluxed for 10 hours, then cooled to room temperature.

Water (1 ml) was added dropwise, followed by 15% aqueous NaOH (1 ml) and water (3 ml) and the solution stirred vigorously for 30 min.

The granular precipitate was filtered and washed several times with ether. The filtrate and washings were dried over sodium sulfate.

Filtration and evaporation of solvent produced white solid (4.26 g, 99.5%). mp.: 140°–141° C. lit.mp 142° C. see:

(a) M. Onda and M. Samamoto, Pharm. Bull (Tokyo), 5, 305 (1957)

(b) M. Protiva, Z. J. Vedjdelek, J. O. Jilek and K. Macek, Coll. Czech. Chem. Comm. 24, 3978 (1959). NMR (CDCl$_3$): $\delta$2.80 (bs, 4 H), 3.45 (s, 2 H), 3.65 (s, 2 H) 6.92–7.40 (m, 9 H), 7.48 (bs, 1 H)

Mass spectrum: (80 eV) m/e (rel intensity) 262 (M+, 19), 261 (5), 144 (24), 143 (100), 142 (4), 91 (19), 40 (21).

EXAMPLE 3 t-butyl methyl 3-benzyl-1,2,3,4,5,6-hexahydroazepino-[4,5b]-indole-5,5-dicarboxylate (VIa)

The chloroindolenine (Va) was prepared by dissolving the N-benzyl amine (IVa) (3.522 g, 13.44 mmol) in 100 ml of dry benzene and cooling to 5° C.

To the cold stirring solution was added dry triethylamine (1.16 g, 10 mmol, 1.6 ml) followed by dropwise addition of t-butyl hypochlorite (1.458 g, 13.44 mmol, 1.6 ml).

The reaction was kept in an ice bath for 1.5 hour, then poured into water at 0° C. (20 ml).

The benzene layer was separated and dried over sodium sulfate. The solution was filtered and the volume reduced to one half by vacuum evaporation. Dry benzene was added to a total volume of ca. 100 ml, then thallium t-butyl methyl malonate (5.28 g, 14 mmol) was added and the stirred solution refluxed for 36 hours. The reaction was cooled to room temperature and filtered through glass fiber paper. The solvent was removed and the residue adsorbed onto silica gel (20 g, Woelm Act III for dry column chromatography). The adsorbed material was placed on top of a 6"×1.5" column of the dry column silica gel and eluted with dichloromethane.

The first 20 ml was discarded and the product was collected in the next 150 ml (3.69 g, 63.3%) recrystallized from aqueous methanol.

mp: 118°–120° C.

IR (CHCl$_3$): 3460, 3440, 3080, 3050, 3020, 2995, 2975, 2940, 2820, 1730, 1610, 1445, 1365, 1250, 1150, 1025, 840, 695 cm$^{-1}$

NMR (CDCl$_3$): $\delta$1.44 (s, 9 H), 2.82 (bs, 4 H), 3.60 (s, 2 H), 3.66 (s, 3 H), 3.76 (s, 2 H), 6.84–7.4 (m, 9 H), 8.36 (bs, 1 H)

Mass spectrum: (80 eV) m/e (rel intensity ) 434 (7), 334 (30), 216 (57), 156 (57), 91 (68), 59 (78), 56 (76), 44 (81), 41 (78), 40 (100).

Analysis calculated for C$_{26}$H$_{30}$N$_2$O$_4$: C, 71.86; H, 6.96; N, 6.45; found: C, 71.97; H, 7.03; N, 6.16

Similarly, the corresponding diethyl and dimethyl azepinoindole derivatives (m.p. respectively 145° C. and 166°–168° C.) are obtained by the condensation of diethyl or dimethyl thallium malonate with the benzylamine (V).

EXAMPLE 4 methyl 3-benzyl-1,2,3,4,5,6-hexahydroazepino-[4,5b]-indole-5-carboxylate (VIIa)

(a) From the t-butyl methyl diester (VIa)

The t-butyl ester (VIa) (1.890 g, 4.35 mmol) was dissolved in 80 ml of 1,2-dichloro-ethane and the system flushed with nitrogen. Anhydrous trifluoroacetic acid (1.6 ml) was added via syringe through a rubber septum. The solution was stirred at reflux for 3.5 hours. The hot reaction mixture was poured into 100 ml of cold (saturated) aqueous sodium carbonate. The layers were separated and the aqueous phase extracted with 50 ml of dichloroethane. The combined organic phases were washed with (saturated) sodium carbonate solution and filtered through phase separating paper onto anhydrous potassium carbonate. Filtration and evaporation of the solvent produced a brown oil which was triturated with ethyl-acetate-heptane to induce crystallization.

The offwhite solid was collected in two crops to yield 1.219 g (84%) of desired decarboxylated amine of formula VII. The compounds was recrystallized twice from aqueous ethanol for analysis.

mp: 135°–135.5° C.

IR (CHCl$_3$): 3480, 3075, 3045, 2940, 2840, 1740, 1600, 1500, 1460, 1435, 1350, 1275, 1230, 1220, 1200, 1163, 1026 cm$^{-1}$

NMR (CDCl$_3$): $\delta$2.94 (bs, 4 H), 3.24 (m, 2 H), 3.76 (s, 3 H), 3.88 (s, 2 H), 4.16 (m, 1 H), 6.97–7.7 (m, 9 H), 8.68 (bs, 1 H)

Mass spectrum: (80 eV) m/e (rel intensity) 334(M+, 37), 216 (100), 156 (61), 91 (49), 42 (32)

Analysis calculated for C$_{21}$H$_{22}$N$_2$O$_2$: C, 75.42; H, 6.63; N, 8.38; found: C, 75.63; H, 6.90; N, 8.41

(b) From the dimethyl diester (VIc)

Diester VIc (9.3 g, 24 mmol), lithium chloride (1.3 g, 30 mmol) and water (620 mg, 34 mmol) were dissolved in anhydrous dimethylformamide (20 ml) under nitrogen and the stirred solution was placed in a preheated (160°–165° C.) oil bath for 1 h. The solution immediately became cloudy and began evolving CO$_2$. After cooling the reaction was poured into water (400 ml) with vigorous stirring. The gummy solid which formed was collected by filtration through glass wool, dissolved in methylene chloride and dried (MgSO$_4$). After concentrating the solution, the product was purified by column chromatography on silica gel, eluting with methylene chloride. This yielded a solid which was recrystallized from hexane to provide VIIa identical with that previously produced (6.6 g, 83%).

EXAMPLE 5 methyl t-butyl 1,2,3,4,5,6-hexahydroazepino-[4,5b]-indole-5,5-dicarboxylate (VI': $R_1=R_2=H$; $R_4=CH_3$; $R_4'=$t-butyl)

A solution of N-benzyl amine (VIa) (202 mg, 0.465 mmol) in dry acetic acid (7.5 ml) was hydrogenated under 1 atm. pressure hydrogen with 5% Pd/C catalyst (22 mg) for 1.5 hour.

The catalyst was filtered and washed with hot methanol.

The solvent was removed from the filtrate by evaporation leaving a light yellow oil which was dissolved in dichloromethane (50 ml). The solution was cooled to 0° C., 10% aqueous NaOH (25 ml) added, and the solution stirred vigorously for 10 min.

The organic phase was separated and dried over anhydrous potassium carbonate. The solution was filtered and the solvent evaporated to a light yellow oil which resisted all attempts at crystallization but was the desired pure debenzylated diester-amine (155 mg, 97%).

IR (CHCl$_3$): 3445, 3435, 3035, 2975, 2915, 1730, 1615, 1455, 1430, 1365, 1250, 1140, 1020, 840, 800 cm$^{-1}$

NMR (CDCl$_3$): δ1.48 (s, 9 H), 2.24 (s, 1 H), 2.96 (m, 2 H), 3.16 (m, 2 H), 3.72 (m, 2 H), 3.78 (s, 3 H), 7.04–7.60 (m, 4 H), 8.88 (bs, 1 H)

Mass spectrum: (80 eV) m/e (rel intensity) 344 (M+, 100%), 245 (82), 229 (56), 216 (96), 215 (87), 203 (87), 171 (67), 155 (74).

EXAMPLE 6 methyl 1,2,3,4,5,6-hexahydroazepino-[4,5b]-indole-5-carboxylate (VIIIa)

The monoester-benzylamine (VIIa) of example 4 (915 mg, 2.74 mmol) was dissolved in 50 ml of glacial acetic acid and 100 mg of 5% Pd/C catalyst added. The mixture was hydrogenated under 1 atm. pressure for 18 hours then filtered through glass fiber paper.

The catalyst was washed with 50 ml of hot methanol and the combined filtrates were evaporated to an oily residue. The residue was dissolved in 75 ml of chloroform and 100 ml of saturated aqueous sodium carbonate was added. The two phase system was stirred vigorously for 15 min. and the layers then separated. The aqueous phase was washed with chloroform and the combined chloroform phases were washed with brine, then filtered through phase separating paper onto anhydrous potassium carbonate. The material was filtered and the solvent evaporated leaving a thick oily residue which was solidified by trituration with ethyl acetate heptane. The material was filtered yielding 532 mg (80%) of desired debenzylated amine (VIIIa).

The mother liquor was chromatographed on silica gel with dichloromethane as eluent, producing another 87 mg of desired material for a combined yield of 93%. The material can be recrystallized from ethyl acetate-heptane.

mp: 138°–139° C.

IR (CHCl$_3$): 3465, 2950, 2925, 1735, 1630, 1460, 1435, 1220, 1160, 1015 cm$^{-1}$

NMR (CDCl$_3$): δ2.20 (bs, 4H), 8.48 (bs, 1H)

Mass spectrum: (80 eV) m/e (rel intensity) 244 (M+, 58), 215 (29), 202 (100), 170 (31), 156 (26), 142 (35), 43 (80), 42 (30)

EXAMPLE 7

(a) methyl 4-dimethoxymethyl-hexanoate

To a solution containing anhydrous methanol (70 ml) and concentrated sulfuric acid (3 drops) was added methyl 4-formylhexanoate (10.2 g, 64.5 mmol). The solution was stirred at room temperature for 24 hours then solid potassium carbonate was added to neutralize the acid. Most of the solvent was evaporated under vacuum, then water (100 ml) was added and the solution extracted twice with hexane (50 ml) then twice with ether. The organic phases were combined and dried over anhydrous magnesium sulfate.

The solvent was evaporated under vacuum yielding the desired acetal with no aldehyde contamination (12.27 g, 93.2%).

bp: 60°–70° C. (Kugelrohr, 0.1 mm)

IR (neat): 2950, 2820, 1730, 1430, 1170, 1105, 1070, 960, 885 cm$^{-1}$

NMR (CDCl$_3$): δ0.88 (t, 3H), 1.24–1.96 (m, 5H), 2.34 (t, 2H) 3.32 (s, 6H), 3.82 (s, 3H), 4.10 (d, 1H)

Mass spectrum: (80 eV) m/e (rel intensity) 204 (M+, 1), 203 (6), 173 (100), 141 (99), 109 (73), 99 (90) 75 (97).

(b) ethyl 4-diethoxymethyl-hexanoate

The ethyl acetal was prepared from the aldehyde in 84% yield in the same manner as the methyl acetal. The ester group exchanges under these conditions.

bp: 90°–100° C. (Kugelrohr, 0.1 mm)

NMR (CDCl$_3$): δ0.95 (t, 3H), 1.23 (t, 6H), 1.33 (t, 3H), 1.25–2.06 (m, 5H), 2.43 (t, 2H), 3.63 (q, 4H) 4.23 (q, 2H), 4.40 (d, 1H).

(c) 4-dimethoxymethyl-1-hexanol

The methyl acetal ester (9.8 g, 48 mmol) end product of example 7a was dissolved in THF (tetrahydrofuran) (20 ml) and added dropwise at 0° C. to an ether solution of LAH (lithiumaluminum hydride) (50 ml of 1 M solution). After addition was completed (ca. 30 min.) the reaction was allowed to warm to room temperature and water (1 ml) was added slowly. Enough 20% aqueous KOH was added to dissolve the solid and the solution extracted five times with ether (25 ml). The ether extracts were washed with brine and dried over anhydrous sodium sulfate. Evaporation of the solvent yielded the desired alcohol (7.86 g, 93%) as a clear colorless liquid.

IR (neat): 3400, 2940, 2830, 1460, 1380, 1190, 1110, 1060, 960 cm$^{-1}$

NMR (CDCl$_3$): δ0.9 (t, 3H), 1.4 (m, 7H), 2.9 (bs, 1H), 3.2 (s, 6H), 3.42 (t, 2H), 4.15 (d, 1H).

(d) 4-diethoxymethyl-1-hexanol

A solution of the ethyl acetal-ester (9.367 g, 38 mmol) end product of example 7b in THF (40 ml) was added at 0° C. to a solution of LAH in ether (40 ml of 1 M solution) over 0.5 hour. The reaction was refluxed 1 hour then allowed to cool to room temperature. Magnesium sulfate heptahydrate (9.86 g, 40 mmol) was added and the reaction stirred vigorously 12 hours. The solid was filtered and washed with ether several times. The combined filtrate and washings were washed with 10% aqueous KOH (10 ml) then brine (10 ml) and dried over anhydrous sodium sulfate. Evaporation of the solvent followed by Kugelrohr distillation (bp 90°–100° C., 0.1 mm) produced the hydroxy-acetal (7.0 g, 90.3%).

IR (neat): 3400, 2985, 2940, 1880, 1460, 1380, 1115, 1065, 730 cm$^{-1}$

NMR (CDCl₃): δ0.93 (t, 3H), 1.23 (t, 6H), 1.16–1.83 (m, 7H) 2.16 (bs, 1H), 3.66 (m, 6H), 4.40 (d, 1H).

(e) 1-bromo-4-dimethoxymethyl-hexane and 1-bromo-4-formylhexane (IXa)

Carbon tetrabromide (1.824 g, 5.5 mmol) and triphenylphosphine (1.443 g, 5.5 mmol) in ether (15 ml) were refluxed 0.5 hour then cooled to room temperature. The 4-dimethoxymethyl-1-hexanol in ether (6 ml) was added dropwise resulting in rapid decolorization of the yellow slurry and precipitation of a buff colored solid. The mixture was filtered through Celite and the solvent removed under vacuum. The residue was placed under high vacuum (ca. $10^{-3}$ mm) to remove the excess carbon tetrabromide and the bromoform by-product. The distillation pot was heated to 50°–60° C. and the distillate collected with the aid of a dry-ice trap. The distillate was the desired bromo-acetal (700 mg, 66%) contaminated with a trace of carbon tetrabromide and bromoform. This compound was used without further purification for hydrolysis.

Hydrolysis of said brom-acetal to the corresponding bromo-aldehyde (1-bromo-4-formyl-hexane) was achieved by stirring in THF/1 N HCl (10:1) (6 ml) at room temperature for 24 hours (94% yield).

For comparison, the bromo-acetal was prepared from the bromo-aldehyde. The bromo-aldehyde (52.4 mg, 0.27 mmol) was dissolved in dry methanol (1 ml) and one crystal of p-toluenesulfonic acid was added. The solution was stirred at room temperature for 48 hours then poured into dichloromethane (15 ml). The solution was washed with saturated aqueous sodium carbonate (5 ml) and dried over anhydrous sodium sulfate. Concentration yielded to acetal (60.4 mg, 93.2%) as a colorless oil with the following characteristics:

IR (neat): 2960, 1460, 1110, 1070 cm$^{-1}$
NMR (CDCl₃): δ0.92 (t, 3H), 1.20–2.04 (m, 7H), 3.38 (s, 6H), 3.40 (t, 2H), 4.16 (d, 1H)
Mass spectrum: (80 eV:m/e (rel intensity) 238, 240 (M+, 0.01) 207, 209, (38, 37), 75 (100).

(f) (+) vincadifformine (Ia)

Method 1

The bromo-aldehyde 1-bromo-4-formyl hexane (194.5 mg, 1 mmol) was dissolved in 6 ml of dry methanol under a nitrogen atmosphere and 123 mg (0.50 mmol) of amine VIIIa was added in 6 ml of methanol. The mixture was stirred at room temperature for 1 hour, then dry triethylamine (0.5 ml) was added and the solution warmed to 40° C. for 12 hours. The reaction was cooled to room temperature and the solvent evaporated. The residue was taken up in CH₂Cl₂ (40 ml) and extracted with (saturated) aqueous sodium carbonate (10 ml). The organic layer was dried over anhydrous potassium carbonate and filtered. The solvent was evaporated and the residue spotted on a preparative TLC plate (2 mm, Merck alumina) and developped with dichloromethane. The band at R$_f$0.4–0.6 was eluted, resulting in 71 mg of pure (+) vincadifformine as a white solid. The alkaloid was recrystallized from 95% ethanol.

mp: 124°–125° C. (lit. 124°–125° C. see J. Kutney, K. Chan, A. Failli, J. M. Fromson, C. Gletsus and V. Nelson, J. Am. Chem. Soc., 90, 3891 (1968))

IR (CHCl₃): 3420, 3360, 2930, 2850, 2775, 1665, 1605, 1470, 1460, 1432, 1290, 1275, 1250, 1235, 1155, 1110, 1045 cm$^{-1}$

NMR (CDCl₃): δ1.6–3.6 (complex m, 18H), 3.76 (s, 3H), 6.74–7.5 (m, 4H), 8.96 (bs, 1H)
UV (EtOH) nm: (log ε) 225 (4.12), 297 (3.15), 327 (4.06)
Mass spectrum: (80 eV) m/e (rel intensity) 338 (M+, 67), 124 (100).

Method 2

The amine VIIIa (125.8 mg, 0.515 mmol) was dissolved in dry benzene (3 ml) and 1-bromo-4-formyl hexane (97.5 mg, 0.505 mmol) was added. The mixture was stirred at 45° C. for 51 hours then dissolved in ether-dichloromethane (1:4). The solution was extracted with 1.0 N HCl and the aqueous phase washed with benzene. The aqueous layer was adjusted to pH 11–12 with 10% aqueous sodium hydroxide and extracted with chloroform. After drying and concentration, a light yellow oil remained (90 mg) which was separated by PTLC (Merck alumina, 5% methanol/95% dichloromethane). The band of R$_f$0.5–0.7 was isolated and eluted yielding (±) vincadifformine (45 mg, 26%) as an oil which crystallized upon seeding.

EXAMPLE 8

±11-methoxyvincadifformine (Ib) (Ervinceine)

(a) Methyl 8-methoxy-1,2,3,4,5,6-hexahydroazepino[4,5-b]indole-5-carboxylate VIIIb A solution of dimethyl 3-benzyl-8-methoxy-1,2,3,4,5,6-hexahydroazepino[4,5-b]indole-5,5-dicarboxylate VIb (1.00 g, 2.37 mmol, obtained from 6-methoxytryptamine by a procedure similar to the one described for VIa), lithium chloride (0.111 g, 2.61 mmol) and 128 µl of water in 10 ml of N,N-dimethylformamide was stirred under nitrogen at 140° C. for 2 h. The mixture, which became heterogeneous in this time was cooled to 20° C., poured into 200 ml of water and extracted with two 75 ml portions of benzene. The benzene solutions were washed with brine, dried over K₂CO₃, filtered and concentrated under vacuum to 0.747 g (86%) of the mono ester VIIb, which has purified by chromatography on silica, eluting with 2.5% methanol in dichloromethane and crystallized from methanol to mp 118°–119° C.

NMR (CDCl₃): δ8.12 (s, 1H), 7.2 (m, 6H), 6.6 (m, 2H), 3.66 (s, 5H), 3.54 (s, 3H), 3.5–3.2 (m, 3H), 3.1–2.6 (m, 4H).

The above N-benzylamino monoester product (0.375 g, 1.03 mmol) and 38 mg of 10% Pd/C catalyst were stirred in acetic acid at 20° C. under 1 atm. of hydrogen for 17 h. After filtration and washing of the catalyst with methanol, the solvents were evaporated under vacuum and the residue dissolved in dichloromethane. Extraction with saturated aq. K₂CO₃ solution, brine, drying over K₂CO₃ filtration and concentration gave 0.276 g (97%) of the amino ester VIIIb, which was crystallized from methanol to mp 166°–167° C.

NMR (CDCl₃): δ8.6 (s, 1H), 7.25 (d, 1H, J=8 Hz), 6.68 (m, 2H), 3.74 (s, 3H), 3.64 (s, 3H), 3.58–2.70 (m, 7H), 2.30 (br s, 1H).

Analysis calculated for C₁₅H₁₈N₂O₃: C, 65.67; H, 6.61; N, 10.21; found: C, 65.45; H, 6.62; N, 10.02

(b) 2-ethyl-5-mesyloxypentanal IXe

To a solution of 2.55 g (0.01 mol) of 4-dimethoxymethyl-1-methanesulfonyloxyhexane in 40 ml of diethyl ether, 20 ml of 1.2 N HCl was added and the mixture stirred at reflux for 12 h. Solid potassium carbonate (3 g) was slowly added, the organic layer separated and the aqueous layer extracted with 25 ml of ether The combined ether solutions were washed with brine, dried over magnesium sulfate, filtered and concentrated to 1.66 g of the aldehyde IXe;

NMR (CDCl$_3$): $\delta$9.57 (d, 1H), 4.20 (m, 2H), 3.00 (s, 3H), 2.23 (m, 1H), 1.88–1.09 (m, 6H), 0.92 (t, 3H)

IR (film)$\nu_{max}$: 2955, 2930, 2870, 2700, 1715, 1450, 1340, 1170, 970–910, 820 cm$^{-1}$ (c) 11-methoxyvincadifformine or ervinceine (Ib)

A solution of the amino ester VIIIb (100 mg, 0.369 mmol), the mesyloxy aldehyde IXe (0.0835 g, 0.401 mmol) and triethylamine (0.122 g, 1.20 mmol) in 5 ml of anhydrous methanol was stirred at 65° C. under nitrogen for 17 h. The solvent was evaporated under vacuum and the residual oil chromatographed by PTLC (1.5 mm silica, 3% methanol in dichloromethane). The band of ervinceine was located by spraying the edge of the plate with ceric ammonium sulfate, producing a characteristic blue color. Elution of ervinceine from the separated band with 1:10 methanol in ether and concentration yielded 0.0981 g (73%) of ervinceine Ib. The product crystallized frm methanol with melting point 90°–92° C.

NMR (CDCl$_3$): $\delta$8.88 (bs, 1H), 7.04 (d, 1H), 6.36 (m, 2H), 3.74 (s, 6H), 3.27–0.69 (m, 14H), 0.55 (t, 3H).

IR (KBr): 3390, 1685, 1620, 1500, 1270 cm$^{-1}$

MS (80 eV) m/e: 368 (M$^+$), 124 (base)

UV (ethanol)$\mu_{max}$ (log $\epsilon$): 249 (4.00), 330 (4.12)

EXAMPLE 9

±Pandoline and epi-pandoline (a) 4-ethyl-5-hydroxypentanoic acid lactone (XII)

Aldehyde-ester XI (15.3 g, 97 mmol) was cooled to 0° C. in anhydrous methanol (125 ml) and sodium borohydride (1.84 g, 48 mmol) was added at a rate such that the reaction stayed below 20° C. The solution was stirred for 30 min. after the addition was completed and then was poured into water. The aqueous solution was extracted with ether (3×75 ml). The combined extracts were washed with saturated brine, dried (MgSO$_4$) and concentrated in vacuo. The oil was taken up in benzene (200 ml) and p-toluenesulfonic acid (1 g) was added. The solution was refluxed for 15 h. using a Dean-Stark trap filled with anhydrous calcium chloride. After cooling the reaction mixture was washed with saturated sodium bicarbonate, dried (MgSO$_4$) and the solvent evaporated. Distillation of the crude material gave lactone XII, bp 70°–75° C. (0.25 mm) (7.2 g, 58%).

IR (neat): 2968, 1730, 1180, 1056 cm$^{-1}$

NMR (CDCl$_3$): $\delta$0.98 (3H, t), 1.2–2.2 (5H, m), 2.58 (2H, m), 4.0 (1H, d of d), 4.35 (1H, m).

(b) Methyl 4-(phenylselenylmethyl)hexanoate XIII

Diphenyl diselenide (3.65 g, 11.7 mmol) was dissolved in freshly distilled dimethylformamide (15 ml) and sodium borohydride (0.89 g, 23 mmol) dissolved in dimethylformamide (10 ml) was carefully added (vigorous evolution of H$_2$) with exclusion of oxygen. The lactone XII (3 g, 23 mmol) was then added and the solution was heated to 120° C. for 8 h. After cooling, the solution was made acidic with 3% HCl and extracted with ether (4×50 ml). The ether solution was washed with water, dried (MgSO$_4$) and concentrated. The crude carboxylic acid was esterified by stirring 15 h. at reflux in anhydrous methanol (20 ml) with trimethyl orthoformate (2.5 g, 23 mmol) and p-toluenesulfonic acid (100 mg). Removal of the methanol in vacuo followed by column chromatography of the residue on silica gel, eluting with hexane until the yellow diselenide band was removed and subsequently with ether gave the pure selenide (3.8 g, 55%). On other runs the yield varied from 25% to 55%. See example 9b′ for spectral data.

(a′) Methyl 4-(methanesulfonyloxymethyl)hexanoate (XII′)

Aldehyde XI (6 g, 38 mmol) was dissolved in methanol (60 ml) and cooled to 0° C. Sodium borohydride (0.75 g, 20 mmol) was added slowly keeping the reaction temperature below 10° C. The solution was stirred an additional 15 min. and was then taken up in methylene chloride and washed with water, saturated brine, and dried (MgSO$_4$). Solvent removal in vacuo at 30° C. gave the crude alcohol derived from the aldehyde XI which was dissolved in methylene chloride (60 ml) with triethylamine (5.2 g, 51 mmol) and cooled to 0° C. Methanesulfonyl chloride (5.5 g, 48 mmol) was added dropwise followed by 30 min. of stirring. An additional 40 ml of methylene chloride was then added and the solution was washed with 3% HCl, saturated aqueous sodium bicarbonate, and dried (MgSO$_4$). Solvent removal followed by distillation, bp 145°–150° C. (0.3 mm), gave the desired pure mesylate XII′ (7.6 g, 81%).

IR (neat): 2965, 1734, 1350, 1175 cm$^{-1}$

NMR (CDCl$_3$): $\delta$1.0 (3H, t), 1.3–1.9 (5H, m), 2.45 (2H, t), 3.1 (3H, s), 3.8 (3H, s), 4.3 (2H, d).

(b′) Methyl 4-(phenylselenylmethyl)hexanoate (XIII)

Diphenyl diselenide (2.8 g, 8.9 mmol) was dissolved in anhydrous dimethylformamide. Sodium borohydride (690 mg, 18 mmol) was carefully added (vigorous evolution of H$_2$) and the solution changed from orange to nearly colorless as the reduction reached completion. The solution was flushed with nitrogen and the mesylate XII′ (2.1 g, 8.5 mmol) was added. The reaction was stirred for 24 h. at room temperature, followed by 3 h. at 45° C. and then poured into water (150 ml). The product was obtained by extracting the aqueous solution with pentane (4×75 ml). The pentane extract was washed with water, dried (MgSO$_4$) and concentrated to a yellow oil. Column chromatography on silica gel, eluting with hexane until the yellow diselenide band came off and then eluting with ether, gave the pure selenide XIII (2.2 g, 90%).

IR (neat): 3060, 2960, 1735, 1578 cm$^{-1}$

NMR (CDCl$_3$): $\delta$0.85 (3H, t), 1.2–1.9 (5H, m), 2.3 (2H, t), 2.9 (2H, d), 3.6 (3H, s), 7.15 (3H, m), 7.44 (2H, m).

(c) Methyl 4-ethyl-4-pentenoate (XIV)

To a solution of selenide XIII (1.8 g, 6.0 mmol) in methylene chloride (15 ml) at −78° C. was added m-chloroperbenzoic acid (1.28 g, 85%, 6.3 mmol). The solution was allowed to warm to room temperature over 30 min. and was then washed with water, saturated sodium carbonate and dried (MgSO$_4$). The methylene chloride was removed in vacuo and the selenoxide was taken up in carbon tetrachloride (15 ml). Triethylamine (640 mg, 6.3 mmol) was added and the solution was refluxed under nitrogen for 2 h. The reaction was taken up in methylene chloride (25 ml), washed with saturated aqueous sodium bicarbonate, dried (MgSO$_4$) and concentrated on a roto-evaporator. The crude olefin XIV was distilled bp 70°–75° C. (25 mm) to give a colorless oil (630 mg, 74%).

IR (neat): 3070, 2960, 1740, 1654, 1160 cm$^{-1}$

NMR (CDCl$_3$): δ1.0 (3H, t), 2.03 (2H, q), 2.2–2.6 (4H, m), 3.64 (3H, s), 4.7 (2H, d).

(d) Methyl 4-ethyl-4-oxyranylpentanoate (XV)

At 0° C. m-chloro-perbenzoic acid (1.25 g, 85%, 6.1 mmol) was added to a stirred solution of olefin XIV (800 mg, 5.6 mmol) in methylene chloride (8 ml). The solution was allowed to warm to room temperature and stirring was continued for 3 h. The solution was then diluted with methylene chloride and washed with saturated aqueous sodium bicarbonate, dried (MgSO$_4$) and concentrated in vacuo. The crude product was purified by distillation, bp 43° C. (0.3 mm) (730 mg, 82%).

IR (neat): 2965, 1735, 1165 cm$^{-1}$

NMR (CDCl$_3$): δ0.95 (3H, t), 1.6 (2H, m), 1.98 (2H, t), 2.4 (2H, t), 2.65 (2H, s), 3.8 (3H, s).

(e) 4-ethyl 4-oxyranyl pentanal IXd is obtained from (XV) by a reduction in dichloromethane with a 1 M solution of DIBAL (diisobutylaminealuminium hydride) in hexane at −75° C. Procedure is identical with the one described for the synthesis of IXc (Example 10b).

(f) Pandoline If and epi-20-pandoline If'

Amine VIIIa (670 mg, 2.8 mmol) and epoxyaldehyde IXd (470 mg, 3.7 mmol) were refluxed under nitrogen in methanol (10 ml) for 1.5 h. Thin layer chromatography on silica gel (CH$_2$Cl$_2$—MeOH, 99:1) showed two main products (visualized as blue spots by spraying with 10% ceric ammonium sulfate on 85% phosphoric acid). The methanol was removed in vacuo and the residue was column chromatographed on silica gel, eluting with methylene chloride-methanol (99:1). The two principal components were obtained. The first, pandoline (If) was recrystallized from acetonitrile (mp 150°–151° C., 290 mg, 30%) and the second, epi-20-pandoline (If') was recrystallized from acetonitrile-water (9:1) (mp 114°–116° C., 205 mg, 21%). Each is identical in all respects except optical rotation with natural samples.

For Pandoline (If):

IR (KBr): 3500, 3400, 2965, 2800, 1678, 1620 cm$^{-1}$

NMR (CDCl$_3$): δ0.96 (3H, t), 1.3–1.7 (4H, m), 1.7–2.3 (4H, m), 2.5–2.8 (3H, m), 2.8–3.1 (4H, m), 3.79 (3H, s), 6.8–7.05 (2H, m), 7.15–7.4 (2H, m), 9.05 (1H, broad)

UV (MeOH) nm 228, 298, 326; MS (m/e) 354 (M+).

Analysis calculated for C$_{21}$H$_{26}$N$_2$O$_3$: C, 71.16, H, 7.39, N, 7.90; found: C, 70.90, H, 7.35, N, 7.78

For epi-20-pandoline (If'):

IR (KBr): 3450 (broad), 3400, 2960, 2805, 1682, 1620 cm$^{-1}$

NMR (CDCl$_3$): δ0.96 (3H, t), 1.2–2.2 (8H, m), 2.45 (2H, m), 2.5–2.95 (3H, m), 3.05 (1H, s), 3.1 (1H, d), 3.78 (3H, s), 6.7–7.0 (2H, m), 7.05–7.3 (2H, m), 8.9 (1H, broad)

UV (MeOH) nm 228, 298, 326; MS (m/e) 354 (M+).

EXAMPLE 10

14-hydroxyvincadifformine Ic and 14-hydroxymethyl-e-norvincadifformine Id (a) Methyl 2-ethyl-4-oxyranylpentanoate To methyl 2-ethyl-4,5-dehydropentanoate (3.85 g, 27 mmol) in methylene chloride (25 ml) at 0° C., was added m-chloroperbenzoic acid (6.5 g, 85%, 32 mmol). The solution was brought to room temperature and stirred for 12 h. The solid which had formed was filtered, washed with methylene chloride and the combined solutions were washed with saturated aqueous sodium carbonate, dried (MgSO$_4$) and concentrated.

Distillation (100° C., 25 mm) of the crude oil gave the epoxide (3.5 g, 81%).

IR (neat): 2960, 1733, 1192, 1172 cm$^{-1}$

NMR (CDCl$_3$): δ0.90 (3H, t), 1.4–2.0 (4H, m), 2.38–2.68 (2H, m), 2.75 (1H, t), 2.95 (1H, m), 3.74 (3H, s).

(b) 2-ethyl-4-oxyranylpentanal IXc

The epoxy-ester (2.08 g, 13.1 mmol) was placed in methylene chloride (20 ml) under nitrogen and cooled to −78° C. With vigorous stirring, diisobutyl aluminum hydride (1.2 equiv., 20% in hexane) was added dropwise over 10 min. The reaction was stirred for an additional 20 min. then quenched with methanol (2 ml) at −78° C. The solution was poured into water and extracted with methylene chloride. The aluminum salts which formed were separated by gravity filtration through glass wool and were washed with methylene chloride. The combined extracts were dried (MgSO$_4$) and concentrated in vacuo. Distillation (60°–65° C., 25 mm) gave 2-ethyl-4-oxyranylpentanal IXc (925 mg, 55%).

IR (neat): 3055, 3023, 2910, 1720, 1450, 1260 cm$^{-1}$

NMR (CDCl$_3$): δ1.0 (3H, t), 1.1–2.1 (4H, m), 2.3–2.6 (2H, m), 2.85 (1H, t), 3.05 (1H, m), 9.85 (1H, d).

(c) 14-hydroxyvincadifformine Ic and isomer Id

Amine VIIIa (500 mg, 2.1 mmol) and epoxyaldehyde IXc (0.5 g, 3.9 mmol) were refluxed under nitrogen in methanol (10 ml) for 2 h. The methanol was removed in vacuo. Compound Id crystallized out after sitting overnight. It was recrystallized from acetonitrile (503 mg, 68%) mp 153°–154° C. The remaining residue was purified by preparative TLC (silica gel, 3% methanol in methylene chloride, rf 0.6 for Ic and 0.15 for Id) yielding a second component (Ic) as an amorphous solid (105 mg, 14%).

For Id:

IR (KBr): 3260, 2950, 1682, 1605 cm$^{-1}$

UV (MeOH): nm 226, 298, 328; MS (m/e) 354 (M+)

For Ic:

IR (film): 3360 (broad), 2950, 2790, 1640, 1600 cm$^{-1}$

UV (MeOH) nm 228, 298, 328; MS (m/e) 354 (M+).

EXAMPLE 11

±Pseudo-vincadifformine Ie and epi-14 pseudovincadifformine Ie'

(a) 4-ethyl-5-hydroxypentanoic acid lactone

Methyl 4-formyl hexanoate (15.3 g, 97 mmol) was cooled to 0° C. in anhydrous methanol (125 ml) and sodium borohydride (1.84 g, 48 mmol) was added at a rate such that the reaction stayed below 20° C. The solution was stirred for 30 min. after the addition was completed and then was poured into water. The aqueous solution was extracted with ether (3×75 ml). The combined extracts were washed with saturated brine, dried (MgSO$_4$) and concentrated in vacuo. The oil was taken up in benzene (200 ml) and p-toluenesulfonic acid (1 g) was added. The solution was refluxed for 15 h. using a Dean-Stark trap filled with anhydrous calcium chloride. After cooling the reaction mixture was washed with saturated sodium bicarbonate, dried (MgSO$_4$) and the solvent evaporated. Distillation of the crude material gave 4-ethyl-5-hydroxypentanoic acid lactone bp 70°–75° C. (0.25 mm) (7.2 g, 58%)

IR (neat): 2968, 1730, 1180, 1056 cm$^{-1}$
NMR (CDCl$_3$): δ0.98 (3H, t) 1.2–2.2 (5H, m), 2.58 (2H, m), 4.0 (1H, d of d), 4.35 (1H, m).

(b) Methyl 4-(bromomethyl)-hexanoate

Anhydrous HBr gas was bubbled into the 4-ethyl-5-hydroxypentanoic acid lactone (3 g, 23 mmol) at 60° C. for 30 min. The solution was allowed to cool and methanol (15 ml) with trimethylorthoformate (2.5 g, 23 mmol) was added. The solution was stirred for 8 h., then concentrated and distilled bp 70°–75° C. (0.1 mm) to produce the desired bromoester (4.3 g, 83%)

IR (neat): 2955, 1733, 1170 cm$^{-1}$
NMR (CDCl$_3$): δ0.98 (3H, t), 1.3–2.0 (5H, m), 2.45 (2H, t), 3.6 (2H, d), 3.82 (3H, s).

(c) 4-(bromomethyl)hexanal IXb

The above mentioned bromoester (1.9 g, 8.5 mmol) was dissolved in anhydrous methylene chloride (20 ml) and cooled with vigorous stirring to −78° C. Diisobutylaluminum hydride (10.2 ml, 1 M in hexane) was added dropwise over 10 min. The solution was stirred for an additional 20 min. at −78° C. and then quenched by the additon of methanol (2 ml). The solution was poured into 3% HCl, extracted with methylene chloride (3×30 ml) and dried (MgSO$_4$). Solvent removal gave a light oil which was purified by distillation, bp 78° C. (0.4 mm) (1.38 g. 84%).

(d) Pseudo vincadifformine Ie (14-ethyl-18,19-dinorvincadifformine) and epi-14-pseudovincadifformine Ie'

Azepino-indole VIIIa (1.00 g, 4.1 mmol) was dissolved in methanol (30 ml) at room temperature and bromoaldehyde IXb (1.0 g, 5.3 mmol) was added. The solution was stirred for 4 hours at which time, triethylamine (1 ml, excess) was added and the solution was heated at 40° C. with stirring for 16 h.

The methanol was removed in vacuo and the residue was taken up in methylene chloride (75 ml), washed with saturated aqueous sodium carbonate, dried (MgSO$_4$) and concentrated. HPLC (using a 10 inch commercial microporacil column with a flow rate of 0.9 ml/min.) eluting with chloroform, showed two components Ie (retention time: 10.3 min.) and Ie' (retention time: 8.5 min.) with a ratio of 4:1 which correspond to the two components (ratio 4:1) in a sample of natural pseudo-vincadifformine. Medium pressure column chromatography (4 ft×1.25 in., silica gel eluting with chloroform allowed isolation of the major isomer as a homogeneous material (by HPLC) which was induced to crystallize by trituration in methanol-water. This was recrystallized from methanol-water (95:5), m.p. 118°–119° C. (170 mg, 12%). Enrichment of the remaining mixture of epimers (460 mg, 34%) by selective crystallization produces mixture of no better than a 1:1 ratio.

For Ie:
IR (KBr): 3365, 2955, 2773, 1666, 1605, 740 cm$^{-1}$
NMR (CDCl$_3$): δ0.95 (3H, t), 1.1–1.6 (4H, m), 1.6–2.15 (4H, m), 2.15–2.65 (3H, m), 2.65–2.95 (4H, m), 3.68 (3H, s), 6.5–6.7 (2H, m), 6.8–7.2 (2H, m), 8.7 (1H, broad)
UV (methanol): nm 228, 298, 328.

For a mixture of Ie and Ie' (ca 1:1) the NMR spectrum shows a shift of absorbances indicating more protons in the region of δ1.6–2.5 and fewer in the region of δ1.1–1.6.

What I claim is:

1. A process for the preparation of ±vincadifformine and related compounds of the formula I:

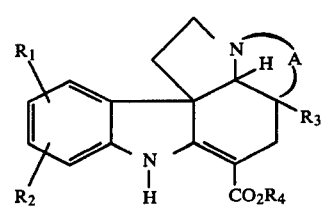

(I)

wherein each of R$_1$ and R$_2$ individually is hydrogen, acyloxy, carbamate, lower alkoxy of one to seven carbon atoms, lower alkyl of one to seven carbon atoms, or halo; R$_3$ and R$_4$ are the same or different and are hydrogen or alkyl having from 1 to 7 carbon atoms; A represents an alkyl chain or unsaturated aliphatic hydrocarbon chain of 2 to 7 carbon atoms and which may be substituted by one or more alkyl, hydroxy or hydroxyalkyl groups having from 1 to 7 carbon atoms, which comprises the steps of:

(a) reacting a tetrahydro-β-carboline of the formula:

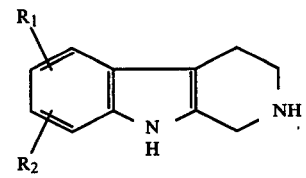

(II)

with benzoyl chloride to form a compound of the formula:

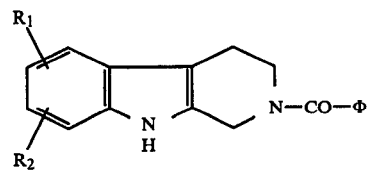

(III)

wherein φ represents a phenyl radical (b) reducing the compound of formula III by means of a reducing agent to form a compound of the formula:

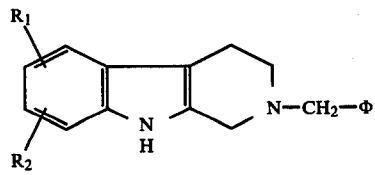

(IV)

(c) chlorinating the compound of formula IV with t-butyl hypochlorite in the presence of triethylamine to form a compound of the formula:

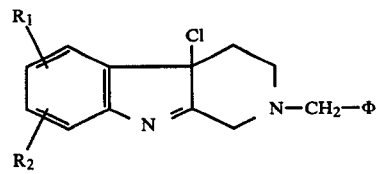

(V)

(d) reacting the compound of formula V with a dialkyl malonate salt of sodium or thallium wherein each alkyl group has 1 to 7 carbon atoms at reflux to form a compound of the formula:

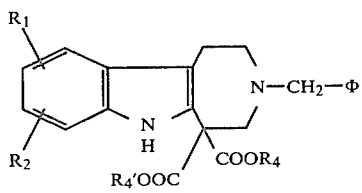
(VI)

(e) decarboalkoxylating partly the compound of formula VI to form a compound of the formula:

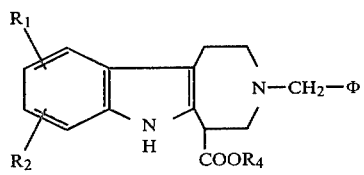
(VII)

(f) hydrogenating the compound of formula VII into a compound of the formula:

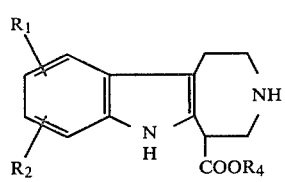
(VIII)

(g) reacting the compound of formula VIII with an aldehyde selected from the group of haloaldehyde, alkylsulfoxyaldehyde, arylsulfoxyaldehyde, epoxyaldehyde or mixture thereof wherein said aldehyde has 3–14 carbon atoms in the presence of triethylamine to yield the desired vincadifformine or related compound of formula I.

2. A process for the preparation of ±vincadifformine and related compounds of the formula:

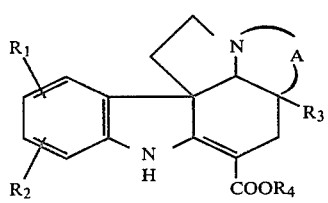
(I)

wherein each of $R_1$ and $R_2$ individually is hydrogen, hydroxy, acyloxy, carbamate, lower alkoxy of 1 to 7 carbon atoms, lower alkyl of 1 to 7 carbon atoms, or halo; $R_3$ and $R_4$ are the same or different and are hydrogen or alkyl of 1 to 7 carbon atoms; A represents an alkyl chain or unsaturated aliphatic hydrocarbon chain of 2 to 7 carbon atoms and which may be substituted by one or more alkyl, hydroxy or hydroxy-alkyl groups of 1 to 7 carbon atoms, which comprises the steps of:

(a) reacting a tetrahydro-β-carboline of the formula:

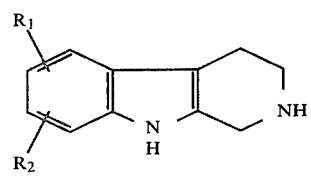
(II)

with benzoyl chloride to form a compound of the formula:

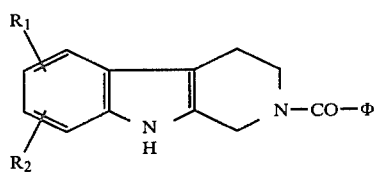
(III)

wherein φ represents a phenyl radical (b) reducing the compound of formula III by means of a reducing agent to form a compound of the formula:

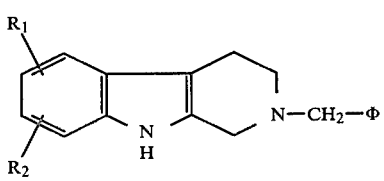
(IV)

(c) chlorinating the compound of formula IV with t-butyl hypochlorite in the presence of triethylamine to form a compound of the formula:

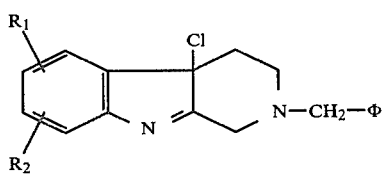
(V)

(d) reacting the compound of formula V with a dialkyl malonate salt of sodium or thallium wherein each alkyl group has 1 to 7 carbon atoms at reflux to form a compound of the formula:

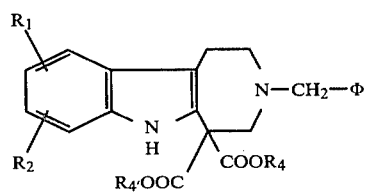
(VI)

(e) hydrogenating the compound of formula VI into a compound of the formula:

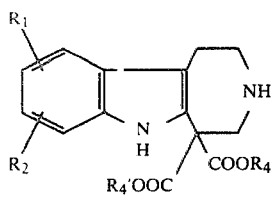

(VI')

(f) decarboalkoxylating partly the compound of formula VI' to form a compound of the formula:

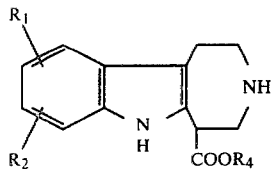

(VIII)

(g) reacting the compound of formula VIII with an aldehyde selected from the group of haloaldehyde, alkylsulfoxyaldehyde, arylsulfoxyaldehyde, epoxyaldehyde or mixture thereof wherein said aldehyde has 3–14 carbon atoms in the presence of triethylamine to yield the desired vincadifformine or related compound of formula I.

3. The process of claim 1 wherein said reducing agent employed in step (b) is lithium aluminum hydride.

4. The process of claim 1 wherein the hydrogenation in step (f) is carried out in the presence of a Pd catalyst.

5. The process of claim 1 wherein the dialkyl malonate salt used in step (d) is thallium t-butyl methyl malonate.

6. The process of claim 5 wherein the decarboalkoxylation of step (e) is effected by treatement using a reagent selected from anhydrous trifluoroacetic acid and anhydrous trifluoracetic anhydride and mixtures thereof.

7. The process of claim 1 wherein the diakyl malonate salt used in step (d) is thallium dimethyl malonate.

8. The process of claim 1 wherein the decarboalkoxylation in step (e) is effected by lithium chloride in dimethylformamide.

9. The process of claim 1 wherein said functionalised aldehyde is selected from the group consisting of 1-bromo-4-formyl-hexane, 4-ethyl-4-oxyranylpentanal, 2-ethyl-4-oxyranylpentanal, 4-bromomethyl hexanal and 2-ethyl-5-mesyloxypentanal.

10. The process of claim 2 wherein said reducing agent employed in step (b) is lithium aluminum hydride.

11. The process of claim 2 wherein the hydrogenating in step (c) is carried out in the presence of a Pd catalyst.

12. The process of claim 2 wherein the diakyl malonate salt used in step (d) is thallium t-butyl methyl malonate.

13. The process of claim 2 wherein the decarboalkoxylation of step (f) is effected by treatment of a reagent selected from anhydrous trifluoroacetic acid and anhydrous trifluoracetic anhydride and mixtures thereof.

14. The process of claim 2 wherein the dialkyl malonate salt used in step (d) is thallium dimethyl malonate.

15. The process of claim 2 wherein the decarboalkoxylation in step (f) is effected by lithium chloride in dimethylformamide.

16. The process of claim 2 wherein said functionalised aldehyde is selected from the group consisting of 1-bromo-4-formyl hexane, 4-ethyl-4-oxyranyl pentanal, 2-ethyl-4-oxyranyl-pentanal, 4-bromomethyl-hexanal and 2-ethyl-5-mesyloxypentanal.

17. A process for preparing a dialkyl 3-benzyl-1,2,3,4,5,6-hexahydroazepino-[4,5b]-indole-5,5-dicarboxylate of the formula:

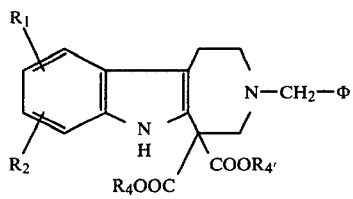

(VI)

wherein each of $R_1$ and $R_2$ individually is hydrogen, hydroxy, acyloxy, carbamate, lower alkoxy of 1 to 7 carbon atoms, lower alkyl of 1 to 7 carbon atoms, or halo, $R_4$ and $R_4$, are the same or different alkyl groups of 1 to 7 carbon atoms which comprises chlorinating 2-benzyl-1,2,3,4-tetrahydro-9H-pyrido [3,4b]-indole of the formula:

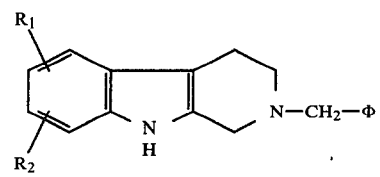

(IV)

with t-butyl hypochlorite under cooling in the presence of dry triethylamine to form a chloroindolenine of the formula:

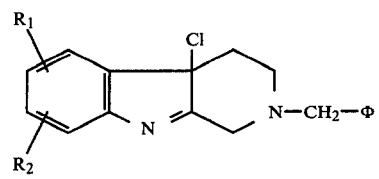

(V)

and immediately reacting said chloroindolenine (formula V) with a dialkyl malonate salt of sodium or thallium wherein each alkyl group has 1 to 7 carbon atoms.

18. A process for preparing ±vincadifformine or related compound of the formula:

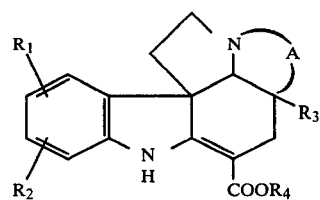

(I)

wherein each of $R_1$ and $R_2$ individually is hydrogen, hydroxy, acyloxy, carbamate, lower alkoxy of 1 to 7 carbon atoms, lower alkyl of 1 to 7 carbon atoms, or halo; $R_3$ and $R_4$ are the same or different and are hydrogen or alkyl of 1 to 7 carbon atoms; A represents an alkyl chain or unsaturated aliphatic hydrocarbon chain having from 2 to 7 carbon atoms and which may be substituted by one or more alkyl, hydroxy, or hydroxyalkyl groups of 1 to 7 carbon atoms, which comprises reacting methyl 1,2,3,4,5,6-hexahydroazepino-[4,5b]-indole-5-carboxylate of the formula:

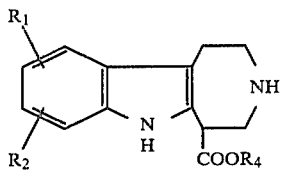
(VIII)

with an aldehyde selected from the group of haloaldehyde, alkylsulfoxyaldehyde, arylsulfoxyaldehyde, epoxyaldehyde or mixture thereof wherein said aldehyde has 3-14 carbon atoms, in a dry methanol under a nitrogen atmosphere in the presence of dry triethylamine at room temperature to yield the desired compound of formula I.

19. A process for preparing ±vincadifformine or related compound of the formula:

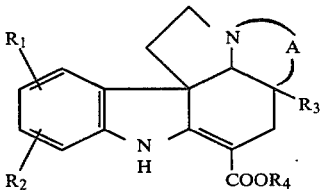
(I)

wherein each of $R_1$ and $R_2$ is hydrogen, hydroxy, acyloxy, carbamate, lower alkoxy of 1 to 7 carbon atoms, lower alkyl of 1 to 7 carbon atoms, or halo; $R_3$ and $R_4$ are the same or different and are hydrogen or an alkyl of 1 to 7 carbon atoms; A represents an alkyl chain or unsaturated aliphatic hydrocarbon chain of 2 to 7 carbon atoms and which may be substituted by one or more alkyl, hydroxy or hydroxy-alkyl groups, having from 1 to 7 carbon atoms, which comprises reacting an alkyl 1,2,3,4,5,6-hexahydroazepino-[4,5b]-indole-5-carboxylate of the formula:

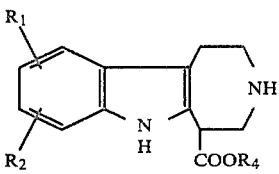
(VIII)

with an aldehyde selected from the group of haloaldehyde, alkylsulfoxyaldehyde, arylsulfoxyaldehyde, epoxyaldehyde or mixture thereof wherein said aldehyde has 3-14 carbon atoms in dry benzene under heating to yield the desired compound (I).

20. The process of claim 1 wherein said aldehyde is a halo or epoxy aldehyde.

21. The process of claim 2 wherein said aldehyde is a halo or epoxy aldehyde.

22. The process of claim 18 wherein said aldehyde is a halo or epoxy aldehyde.

23. The process of claim 19 wherein said aldehyde is a halo or epoxy aldehyde.

24. The process of claim 1 wherein A represents an alkyl chain or unsaturated aliphatic hydrocarbon chain of 2-3 carbon atoms and which may be substituted by one or more alkyl, hydroxy or hydroxy-alkyl groups having from 1 to 7 carbon atoms.

* * * * *